United States Patent
Raghuraman et al.

(10) Patent No.: US 11,479,642 B2
(45) Date of Patent: *Oct. 25, 2022

(54) PROCESS OF MANUFACTURING POLYOLS

(71) Applicants: Dow Global Technologies LLC, Midland, MI (US); Northwestern University, Evanston, IL (US)

(72) Inventors: Arjun Raghuraman, Pearland, TX (US); William H. Heath, Lake Jackson, TX (US); Sukrit Mukhopadhyay, Midland, MI (US); Heather A. Spinney, Midland, MI (US); David R. Wilson, Midland, MI (US); Anthony P. Gies, Lake Jackson, TX (US); Manjiri R. Paradkar, Lake Jackson, TX (US); Justin M. Notestein, Evanston, IL (US); SonBinh T. Nguyen, Evanston, IL (US)

(73) Assignees: Dow Global Technologies LLC, Midland, MI (US); Northwestern University, Evanston, IL (US)

( * ) Notice: Subject to any disclaimer, the term of this patent is extended or adjusted under 35 U.S.C. 154(b) by 279 days.

This patent is subject to a terminal disclaimer.

(21) Appl. No.: 16/644,284

(22) PCT Filed: Sep. 14, 2018

(86) PCT No.: PCT/US2018/050985
§ 371 (c)(1),
(2) Date: Mar. 4, 2020

(87) PCT Pub. No.: WO2019/055725
PCT Pub. Date: Mar. 21, 2019

(65) Prior Publication Data
US 2020/0231738 A1    Jul. 23, 2020

Related U.S. Application Data

(60) Provisional application No. 62/635,631, filed on Feb. 27, 2018, provisional application No. 62/558,422, filed on Sep. 14, 2017, provisional application No. 62/558,409, filed on Sep. 14, 2017.

(51) Int. Cl.
| | |
|---|---|
| C08G 65/26 | (2006.01) |
| B01J 31/02 | (2006.01) |
| C08G 18/48 | (2006.01) |
| B01J 31/14 | (2006.01) |
| C07C 41/03 | (2006.01) |

(52) U.S. Cl.
CPC ...... C08G 65/2609 (2013.01); B01J 31/0275 (2013.01); B01J 31/143 (2013.01); C08G 18/4841 (2013.01); C08G 65/266 (2013.01); C08G 65/2654 (2013.01); C08G 65/2669 (2013.01); C08G 65/2684 (2013.01); *B01J 2231/20* (2013.01); *B01J 2531/004* (2013.01); *C07C 41/03* (2013.01)

(58) Field of Classification Search
CPC .............. C08G 65/2609; C08G 65/266; C08G 65/2654; C08G 65/2684
See application file for complete search history.

(56) References Cited

U.S. PATENT DOCUMENTS

| | | |
|---|---|---|
| 6,482,993 B1 | 11/2002 | Hofmann et al. |
| 6,531,566 B1 | 3/2003 | Satake |
| 6,624,321 B2 * | 9/2003 | Denninger ........... B01J 31/0257 526/273 |
| 9,040,657 B2 | 5/2015 | Laitar et al. |
| 9,340,640 B2 * | 5/2016 | Hirano ............... C08G 18/4211 |
| 9,388,271 B2 * | 7/2016 | Nakaminami ....... C08G 18/485 |

(Continued)

FOREIGN PATENT DOCUMENTS

| | | |
|---|---|---|
| EP | 1340780 A1 | 9/2003 |
| WO | 9921903 A1 | 5/1999 |

(Continued)

OTHER PUBLICATIONS

Chakraborty, D et al., Catalytic Ring-Opening Polymerization of Propylene Oxide by Organoborane and Aluminum Lewis Acids. Macromolecules 2003, 36, 5470-5481.
Chandrasekhar, S. et al., Highly efficient cleavage of epoxides catalyzed by B(C6F5)3. Tetrahedron Lett. 2002, 43, 3801-3803.
PCT/US2018/050991, International Search Report and Written Opinion dated Nov. 22, 2018.
Office Action from corresponding Chinese 201880066977.X Patent Application, dated Jun. 10, 2022.

*Primary Examiner* — Michael L Leonard

(57) ABSTRACT

A method of producing a polyether polyol that includes reacting a low molecular weight initiator with one or more monomers in the presence of a polymerization catalyst, the low molecular weight initiator having a number average molecular weight of less than 1,000 g/mol and a nominal hydroxyl functionality at least 2, the one or more monomers including at least one selected from propylene oxide and butylene oxide, and the polymerization catalyst being a Lewis acid catalyst having the general formula $M(R^1)_1(R^2)_1(R^3)_1(R^4)_{0 \text{ or } 1}$. Whereas, M is boron, aluminum, indium, bismuth or erbium, $R^1$, $R^2$, and $R^3$ each includes a same fluoroalkyl-substituted phenyl group, and optional $R^4$ includes a functional group or functional polymer group. The method further includes forming a polyether polyol having a number average molecular weight of greater than the number average molecular weight of the low molecular weight initiator in the presence of the Lewis acid catalyst.

8 Claims, 1 Drawing Sheet

(56) References Cited

U.S. PATENT DOCUMENTS

| | | |
|---|---|---|
| 2002/0128521 A1 | 9/2002 | Priou et al. |
| 2004/0030093 A1 | 2/2004 | Sakurai et al. |
| 2011/0230581 A1 | 9/2011 | Klescewski et al. |
| 2017/0240702 A1* | 8/2017 | Raghuraman ........ C08G 65/269 |

FOREIGN PATENT DOCUMENTS

| | | |
|---|---|---|
| WO | 2002057209 A1 | 7/2002 |
| WO | 2008123323 A1 | 10/2008 |
| WO | 2012134849 A1 | 10/2012 |
| WO | 2016064698 A1 | 4/2016 |

* cited by examiner

PROCESS OF MANUFACTURING POLYOLS

FIELD

Embodiments relate to methods of manufacturing polyols using at least a Lewis acid catalyst, polyols prepared using at least the Lewis acid catalyst, and/or polyurethane products prepared using the polyols prepared using at least the Lewis acid catalyst.

INTRODUCTION

Polyether polyols are produced by polymerizing an alkylene oxide in the presence of a starter compound and a catalyst. The starter compound has one or more functional groups the alkylene oxide can react with to begin forming polymer chains. The starter compound may influence the molecular weight and establish the number of hydroxyl groups that the resultant polyether polyol will have.

With respect to the catalyst for forming polyether polyols, manufacturing is moving toward the use of a double-metal cyanide (DMC) catalyst in place of an alkali metal catalyst (such as a KOH-based catalyst). A disadvantage of DMC catalysts is that they may activate slowly, as is taught in U.S. Pat. No. 9,040,657. In particular, preparation of polyether polyols using the DMC catalyst may begin with a stage of the reaction known as the catalyst induction period. During this stage of the reaction, the DMC catalyst is believed to become converted in situ from an inactive form into a highly active form that rapidly polymerizes the alkylene oxide as long as the catalyst remains active. This catalyst induction period is typically an indeterminate period of time following the first introduction of alkylene oxide to the reactor. It is common to introduce a small amount of alkylene oxide at the start of the polymerization process and then wait until the catalyst has become activated (as indicated, e.g., by a drop in reactor pressure due to the consumption of the initial alkylene oxide that had been charged into the reactor) before continuing with the alkylene oxide feed. Very little or no polymerization occurs until the catalyst has become activated, such that long activation times have a direct negative impact on the productivity of the process. It is sometimes the case that the catalyst does not become activated at all. Such a failure of the catalyst to activate may result in the abandonment of the attempt, and the process is started over again from the beginning. As such, the activation process results in some loss of productivity under the best circumstances, and under the worst circumstances can cause a loss of the entire batch of starting mixture. Thus, the reduction or elimination of the induction period at the start of the alkoxylation reaction is seen to be highly desirable.

The disadvantages of the use of conventional Lewis acids such as boron trifluoride to polymerize epoxides is well-known, e.g., as taught in U.S. Pat. No. 6,624,321. For example, use of such conventional Lewis acids as catalysts may lead to the formation of volatile low molecular weight cyclic ethers, may require high levels of catalyst loading (which ultimately require the need for a later process stage to remove catalyst from the resultant product), and may lead to catalyst decomposition during which release of a highly corrosive HF side-product and incorporation of fluorine atoms in the backbone of the polymerization product may occur. Further, boron trifluoride is regarded as hazardous material that is also moisture sensitive and difficult to handle.

The use of tris(pentafluorophenyl)borane catalyst during ring-opening polymerization of an alkylene oxide is taught, e.g., in U.S. Pat. No. 6,531,566. The tris(pentafluorophenyl)borane catalyst provides several advantages over conventional Lewis acids such as boron trifluoride. For example, the tris(pentafluorophenyl)borane catalyst is not corrosive, easy to handle, and appreciably more active. However, use of tris(pentafluorophenyl)borane as an alkoxylation catalyst results in an undesirable side-reaction leading to formation of aldehydes and acetal linkages in the polyol backbone.

The use of a dual catalyst package for producing a polyol having a high primary hydroxyl group content, which includes a DMC catalyst and a Lewis acid catalyst is disclosed, e.g., in International Publication No. WO 2016/064698. This method may minimize the residence time of the Lewis acid step and enable the production of high molecular weight polyether polyols. Nevertheless, there is a need to be able to change the selectivity of the Lewis acid catalyst itself, e.g., to select other specific properties for the resultant polyether polyols. Further, high loading of tris(pentafluorophenyl)borane catalyst could potentially require further finishing of the resultant polyether polyols.

Therefore, improvements are sought with respect to minimizing side-reactions such as those that produce acetals and/or aldehydes, while still allowing for precise control of the polymerization reaction and optionally the production of non-finishing polyols (i.e., polyols that do not require further finishing).

SUMMARY

Embodiments may be realized by providing a method of producing a polyether polyol that includes reacting a low molecular weight initiator with one or more monomers in the presence of a polymerization catalyst, the low molecular weight initiator having a nominal hydroxyl functionality at least 2, the one or more monomers including at least one selected from propylene oxide and butylene oxide, and the polymerization catalyst being a Lewis acid catalyst having the general formula $M(R^1)_1(R^2)_1(R^3)_1(R^4)_{0\ or\ 1}$. Whereas, M is boron, aluminum, indium, bismuth or erbium, $R^1$, $R^2$, and $R^3$ each includes a same fluoroalkyl-substituted phenyl group, and optional $R^4$ includes a functional group or functional polymer group. The method further includes forming a polyether polyol having a number average molecular weight of greater than the number average molecular weight of the low molecular weight initiator in the presence of the Lewis acid catalyst.

BRIEF DESCRIPTION OF THE DRAWINGS

Features of the embodiments will become more apparent to those of ordinary skill in the art by describing in detail exemplary embodiments thereof with reference to the attached drawings in which.

DETAILED DESCRIPTION

Figure 1:
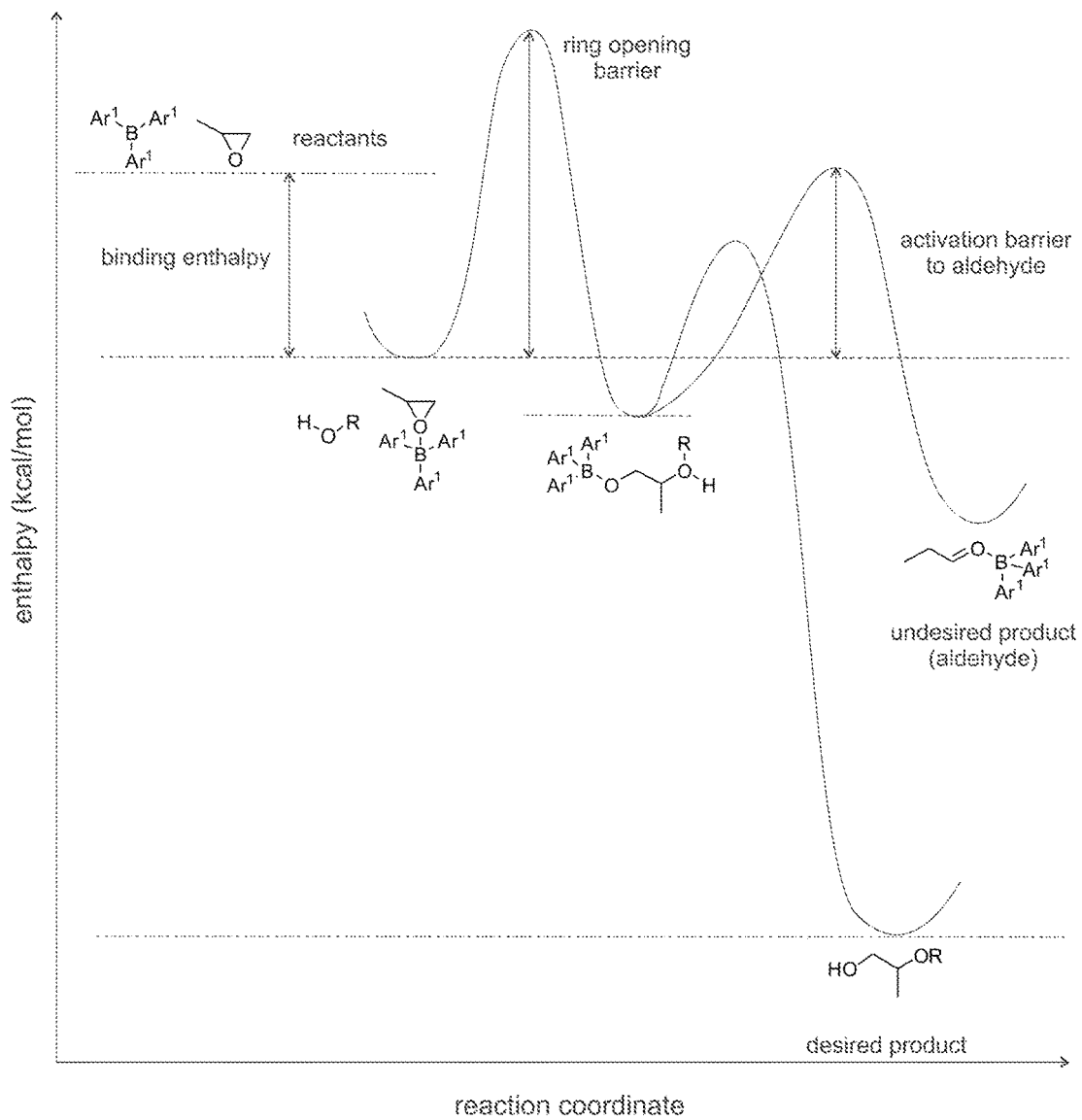
FIG. 1 illustrates an exemplary diagram of reaction coordinate to enthalpy for aldehyde formation.

As discussed in International Publication No. WO 2012/091968, certain Lewis acids that may essentially require no activation time have been evaluated as polymerization catalysts. However, some Lewis acids may become deactivated rapidly and may not be capable of producing high molecular weight polymers or of obtaining high conversions of alkylene oxides to polymer. Further, high amounts of alkaline catalysts, such as sodium hydroxide may require treatment such as filtration and/or acid finishing/neutralization (e.g., as discussed in U.S. Pat. No. 5,468,839) to reduce the base content of the resultant product. The use of a sufficiently low amount of Lewis acid catalysts and optionally a DMC catalyst may eliminate the need for such treatment, while also providing for control and/or selectivity. However, certain Lewis acids may promote undesirable side reactions. The presence of certain side products in a polyol product may necessitate performing an additional finishing step on the resultant product.

Embodiments relate to certain Lewis acid catalysts, and processes using such Lewis acid catalysts, that may provide advantages with respect to minimizing side reactions such as those that produce aldehydes and/or acetals, while still allowing for precise control of the polymerization reaction. Embodiments may relate to providing polyol polymers having a desirably low level of aldehydes and acetals. The polyols are derived from at least one alkylene oxide selected from propylene oxide and butylene oxide and may optionally essentially exclude intended addition of ethylene oxide. By Lewis acid it is meant a substance that can accept a pair of electrons. In other words, a Lewis acid is an electron-pair acceptor.

During the polymerization process to form a polyether polyol, some Lewis acid catalysts, such as the tris(pentafluorophenyl)borane catalyst, may have a disadvantage in that certain side reactions may occur at undesirable levels (depending on the outcome desired). An example of such side reactions is the tris(pentafluorophenyl)borane catalyst-assisted formation of propionaldehyde as shown below in Schematic 1, which may occur in the presence of alcohols and may lead to the lack of desired chemoselectivity for the resultant polyether polyol.

Schematic 1

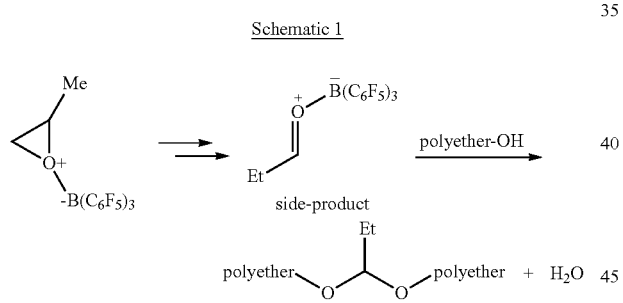

Further, the propionaldehyde-alcohol coupling, such as shown above, may result in higher molecular weight species as compared to when the coupling is not present and/or may make molecular weight control challenging especially at a commercial scale. Also, the water byproduct that results from the coupling reaction could potentially consume monomer and result in the formation of diols and/or alter the catalytic activity of the tris(pentafluorophenyl)borane catalyst. Further, when the resultant product is used to form a polyurethane polymer, acetal linkages may be found at undesirable levels, which could potentially degrade over the life of the polyurethane polymer-based product depending on the application.

Accordingly, in exemplary embodiments, a reaction system for forming a polyether polyol (such as a propylene oxide based polyol, a butylene oxide based polyol, or a combination thereof) uses a Lewis acid catalyst (e.g., in a low amount such that filtration and acid finishing/neutralization are not required for the resultant polyether polyol) that minimizes side reactions and optionally may be combined with a DMC catalyst. For example, it is proposed to use triarylborane catalysts that have fluoroalkyl-substituted phenyl groups, which may allow for improvements with respect to selectively minimizing side reactions such as those that produce acetals and/or aldehydes and/or for precise control of the polymerization reaction.

In particular, it has been found that triarylborane catalysts containing fluoroalkyl substituents may significantly decrease the side-reactions leading to lower acetal linkages in the backbone. It is believed that the fluoroalkyl groups may impart unique properties to the metal (such as boron) active center. For example, the Hammett constant ($\sigma$) for a fluorine group in the para position $\sigma_p$=0.06 whereas that for a $CF_3$ group in the para position is 0.54. As such, a $CF_3$ group may act as a unique electron withdrawing group, which is in part related to the inability of F atoms to donate into the ring.

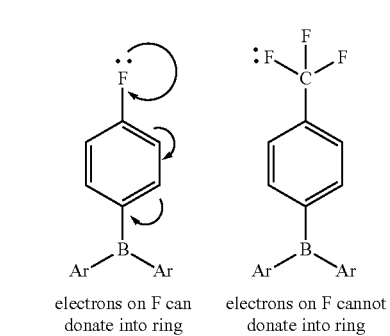

electrons on F can donate into ring electrons on F cannot donate into ring

Embodiments relate to forming a polyether polyol (e.g., a propylene oxide- and/or butylene oxide-based polyol) with a low amount of acetal linkages. The polyether polyol may have a relatively high number average molecular weight (i.e., greater than 500 g/mol, greater than 1000 g/mol, greater than 2,500 g/mol such as from 2,600 g/mol to 12,000 g/mol, 3,000 g/mol to 6,000 g/mol, etc.)

According to exemplary embodiments, a catalyst component for forming the polyether polyol may utilize the at least one Lewis acid catalyst and optionally the DMC catalyst. For example, the at least one Lewis acid catalyst may be used without the DMC catalyst, or the DMC catalyst and the Lewis acid catalyst may be simultaneously or sequential added. For example, in a DMC-Lewis acid dual catalyst system, a polymerization method may include initially adding a DMC catalyst and later adding the Lewis acid catalyst that is separately provided and allowed to react at a lower temperature than the temperature at which the DMC catalyst was added. The Lewis acid catalyst may be active at a lower temperature range (e.g., from 60° C. to 115° C.) than a temperature range at which the DMC catalyst may be active (e.g., from 125° C. to 160° C.).

Polyether polyols include polyols that have multiple ether bonds. Exemplary polyether polyols include polyether hybrid polyols (such as polyether carbonate polyols and polyether ester polyols). The polyether polyols are produced by polymerizing an alkylene oxide component that includes at least one alkylene oxide and an initiator component that includes at least one initiator compound. The initiator compound has one or more functional groups at which the alkylene oxide can react to begin forming the polymer chains. The main functions of the initiator compound are to provide molecular weight control and to establish the number of hydroxyl groups that the monol or polyol product will have. The polyether carbonate may be produced by polymerizing carbon dioxide, at least one alkylene oxide, and an initiator compound. The polyether ester may be produced by polymerizing at least one alkylene oxide with a carboxylic acid initiator.

Lewis Acid Catalyst

According to exemplary embodiments, the Lewis acid catalyst has the general formula $M(R^1)_1(R^2)_1(R^3)_1(R^4)_{0\ or\ 1}$, whereas M is boron, aluminum, indium, bismuth or erbium, $R^1$, $R^2$, and $R^3$ are each a fluoroalkyl-substituted phenyl group, and optional $R^4$ is a functional group or functional polymer group. The M in the general formula may exist as a metal salt ion or as an integrally bonded part of the formula. $R^1$, $R^2$, and $R^3$ are each a fluoroalkyl-substituted phenyl group. $R^1$, $R^2$, and $R^3$ are each the same fluoroalkyl-substituted phenyl group.

$R^1$, $R^2$, and $R^3$ may include the fluoroalkyl-substituted phenyl group or may consist essentially of the fluoroalkyl-substituted phenyl group. Similarly, $R^4$ may include the functional group or functional polymer group, or consist essentially of the $R^4$ is the functional group or functional polymer group.

With respect to $R^1$, $R^2$, and $R^3$, by fluoroalkyl-substituted phenyl group it is meant a phenyl group that includes at least one hydrogen atom replaced with a fluoroalkyl group, which is an alkyl group with at least one hydrogen atom replaced with a fluorine atom. For example, the fluoroalkyl group may have the structure $C_nH_mF_{2n+1-m}$, whereas n is greater than or equal to 1 and less than or equal to 5. Also, m is a number that reflects a balance of the electrical charges to provide an overall electrostatically neutral compound, e.g., can be zero, one or greater than one. The phenyl group of the fluoroalkyl-substituted phenyl may be substituted to include other groups in addition to the at least one fluoroalkyl group, e.g., a fluorine atom and/or chlorine atom that replaces at least one hydrogen of the phenyl group. For example, $R^1$, $R^2$, and $R^3$ may be a fluoro/chloro-fluoroalkyl-substituted phenyl group (meaning one fluoro or chloro group and at least one fluoroalkyl group are substituted on the phenyl group), difluoro/chloro-fluoroalkyl-substituted phenyl group (meaning two fluoro, two chloro, or a fluoro and chloro group and at least one fluoroalkyl group are substituted on the phenyl group), trifluoro/chloro-fluoroalkyl-substituted phenyl group (meaning three fluoro, three chloro, or a combination of fluoro and chloro groups totaling three and at least one fluoroalkyl group are substituted on the phenyl group), or tetrafluoro/chloro-fluoroalkyl-substituted phenyl group (meaning four fluoro, four chloro, or a combination of fluoro and chloro groups totaling four and one fluoroalkyl group are substituted on the phenyl group).

With respect to optional $R^4$, the functional group or functional polymer group may be a Lewis base that forms a complex with the Lewis acid catalyst (e.g., a boron based Lewis acid catalyst) and/or a molecule or moiety that contains at least one electron pair that is available to form a dative bond with a Lewis acid. The Lewis base may be a polymeric Lewis base. By functional group or functional polymer group it is meant a molecule that contains at least one of the following: water, an alcohol, an alkoxy (examples include a linear or branched ether and a cyclic ether), a ketone, an ester, an organosiloxane, an amine, a phosphine, an oxime, and substituted analogs thereof. Each of the alcohol, linear or branched ether, cyclic ether, ketone, ester, alkoxy, organosiloxane, and oxime may include from 2-20 carbon atoms, from 2-12 carbon atoms, from 2-8 carbon atoms, and/or from 3-6 carbon atoms.

For example, the functional group or functional polymer group may have the formula (OYH)n, whereas O is O oxygen, H is hydrogen, Y is H or an alkyl group, and n is an integer (e.g., an integer from 1 to 100). However, other known functional polymer groups combinable with a Lewis acid catalyst such as a boron based Lewis acid catalyst may be used. Exemplary cyclic ethers include tetrahydrofuran and tetrahydropyran. Polymeric Lewis bases are moieties containing two or more Lewis base functional groups such as polyols and polyethers based on polymers of ethylene oxide, propylene oxide, and butylene oxide. Exemplary polymeric Lewis bases include ethylene glycol, ethylene glycol methyl ether, ethylene glycol dimethyl ether, diethylene glycol, diethylene glycol dimethyl ether, triethylene glycol, triethylene glycol dimethyl ether, polyethylene glycol, polypropylene glycol, and polybutylene glycol.

Exemplary Lewis acid catalysts have the following structure in which each of $Ar^1$ includes at least one fluoroalkyl (Y) group substituted on a phenyl group and optionally at least one fluoro or chloro (X) substituted on the phenyl group:

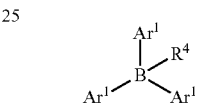

X = F, Cl
Y = fluoroalkyl group containing 1-5 carbons
$R^4$ = optional and is a functional group or a functional polymer group

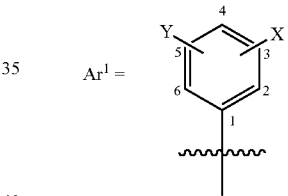

Y can be attached to positions 3, 4, 5 a combination of these
X can be attached to positions 2, 3, 4, 5 or 6 or a combination of these Whereas each $Ar^1$ has the same structure. Exemplary structures for $Ar^1$ are the following, referred to as Set 1 structures:

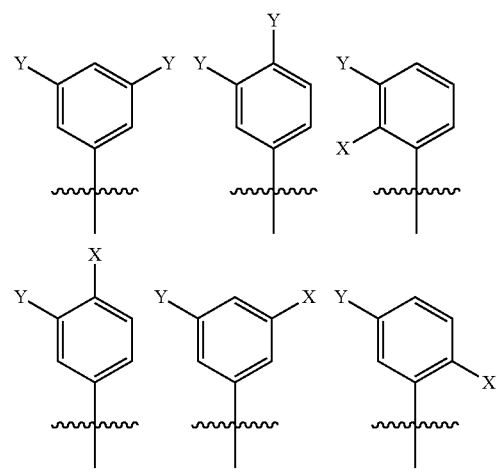

According to exemplary embodiments, the Lewis acid catalyst is a boron based Lewis acid catalyst that has the general formula $B(R^1)_1(R^2)_1(R^1)_1(R^4)_{0\ or\ 1}$, whereas $R^1$, $R^2$, and $R^3$ are the fluoroalkyl-substituted phenyl group, and optionally $R^4$ is the functional group or functional polymer group. For example, the fluoroalkyl-substituted phenyl group is a 2,4-difluoro-3-(trifluoromethyl)phenyl group. For example, the fluoroalkyl-substituted phenyl group is a 2,4,6-trifluoro-3-(trifluoromethyl)phenyl group. In exemplary embodiments, at least one of $R^1$ or $R^2$ or $R^3$ is a 3,4- or 3,5-bis(fluoroalkyl)-substituted phenyl group (e.g., a 3,4 or 3,5-bis(trifluoromethyl)-substituted phenyl group). For example, $R^4$ is a cyclic ether having 3-10 carbon atoms.

Exemplary structures for the Lewis acid catalysts, where M is Boron are shown below:

While the above illustrates exemplary structures that include boron, similar structures may be used that include other metals such as aluminum, indium, bismuth, and/or erbium.

Without intending to be bound by this theory, certain $R^4$ may help improve shelf life of the catalyst, e.g., without significantly compromising catalyst activity when utilized in a polymerization reaction. For example, the catalyst comprising M, $R^1$, $R^2$, and $R^3$ may be present in the form with the optional $R^4$ (form $M(R^1)_1(R^2)_1(R^3)_1(R^4)_1$) or without the optional $R^4$ (form $M(R^1)_1(R^2)_1(R^3)_1$). The optional $R^4$ may dissociate step-wise from $M(R^1)_1(R^2)_1(R^3)_1(R^4)_1$ to give free $M(R^1)_1(R^2)_1(R^3)_1$, as shown below for M=B, which free $M(R^1)_1(R^2)_1(R^3)_1$ may be a catalyst for an alkoxylation/polymerization process, and/or may dissociate from $M(R^1)_1(R^2)_1(R^3)_1(R^4)_1$ in a concerted or other single-step process with the alkylene oxide to give a catalyst for an alkoxylation/polymerization process.

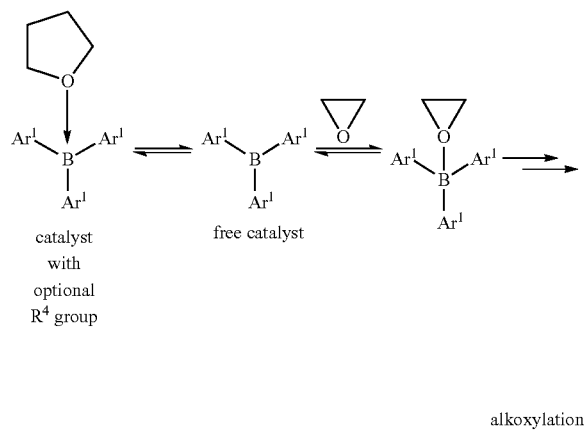

The ability of the optional $R^4$ group to protect the boron, aluminum, indium, bismuth and erbium center from inadvertent decomposition reactions may be related to a decrease in the accessible volume of the center. The accessible volume of the center is defined as the volume around the atom, such as the boron atom, that is available for interaction with other molecules.

| Catalyst | Accessible volume of boron (%) |
|---|---|
| 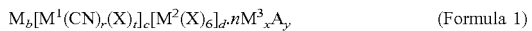 | 25 |

| Catalyst | Accessible volume of boron (%) |
|---|---|
|  | 10 |

Suitable $R^4$ groups that can help increase catalyst shelf stability, e.g., without compromising catalyst activity, include diethyl ether, cyclopentyl methyl ether, methyl tertiary-butyl ether, tetrahydrofuran, 2-methyltetrahydrofuran, tetrahydropyran, 1,4-dioxane, acetone, methyl isopropyl ketone, isopropyl acetate, and isobutyl acetate.

The Lewis acid catalyst used in exemplary embodiments may be a blend catalyst that includes one or more Lewis acid catalysts (e.g., each having the general formula $B(R^1)_1(R^2)_1(R^3)_1(R^4)_{0 \text{ or } 1}$) and optionally at least one other catalyst (e.g., such as catalysts known in the art for producing polyether polyols). The blend catalyst may optionally include other catalysts, in which the one or more Lewis acid catalysts having the general formula $B(R^1)_1(R^2)_1(R^3)_1(R^4)_{0 \text{ or } 1}$ account for at least 25 wt %, at least 50 wt %, at least 70 wt %, at least 75 wt %, at least 80 wt %, at least 85 wt %, at least 90 wt %, at least 95 wt %, at least 99 wt %, etc., of the total weight of the blend catalyst.

DMC Catalyst

The catalyst component may optionally include DMC catalysts. Exemplary DMC catalysts and method of producing DMC catalyst are described, e.g., in U.S. Pat. Nos. 3,278,457, 3,278,458, 3,278,459, 3,404,109, 3,427,256, 3,427,334, 3,427,335, and 5,470,813. An exemplary type of DMC catalyst is a zinc hexacyanocobaltate catalyst complex. The mDMC catalyst complexes may be prepared using modified methods of forming the DMC catalysts. The DMC catalyst, e.g., ones that are known in the art, may be used in the catalyst system that includes the Lewis acid catalyst. The DMC catalyst may be the first or second catalyst that is provided.

For example, the DMC catalysts may be represented by the Formula 1:

$$M_b[M^1(CN)_r(X)_t]_c[M^2(X)_6]_d \cdot nM^3_xA_y \qquad \text{(Formula 1)}$$

wherein M and $M^3$ are each metals; $M^1$ is a transition metal different from M. $X^1$ represents a group other than cyanide that coordinates with the $M^1$ ion. $M^2$ is a transition metal. $X^2$ represents a group other than cyanide that coordinates with the $M^2$ ion. $X^1$ or $X^2$ may each independently be a halogen, sulfate, nitrate, phosphate, carbonate, or chlorate. In exemplary embodiments, $X^1$ and $X^2$ are the same and are chloride. $A^1$ represents an anion; b, c and d are numbers that reflect an electrostatically neutral complex; r is from 4 to 6; t is from 0 to 2; x and y are integers that balance the charges in the metal salt $M^3_xA_y$, and n is zero or a positive integer. For example, n is from 0.01 to 20. The foregoing formula does not reflect the presence of neutral complexing agents such as t-butanol which are often present in the DMC catalyst complex.

Referring to Formula (I), M and $M^3$ each are a metal ion independently selected from (e.g., from the group consisting of): $Zn^{2+}$, $Fe^{2+}$, $Co^{+2+}$, $Ni^{2+}$, $Mo^{4+}$, $Mo^{6+}$, $Al^{+3+}$, $V^{4+}$, $V^{5+}$, $Sr^{2+}$, $W^{4+}$, $W^{6+}$, $Mn^{2+}$, $Sn^{2+}$, $Sn^{4+}$, $Pb^{2+}$, $Cu^{2+}$, $La^{3+}$ and $Cr^{3+}$. Exemplary embodiments include at least $Zn^{2+}$. Further, $M^1$ and $M^2$ each are a metal ion independently selected from (e.g., from the group consisting of): $Fe^{3+}$, $Fe^{2+}$, $Co^{3+}$, $Co^{2+}$, $Cr^{2+}$, $Cr^{3+}$, $Mn^{2+}$, $Mn^{3+}$, $Ir^{3+}$, $Ni^{2+}$, $Rh^{3+}$, $Ru^{2+}$, $V^{4+}$, $V^{5+}$, $Ni^{2+}$, $Pd^{2+}$, and $Pt^{2+}$. Among the foregoing, those in the plus-three oxidation state may be used for the $M^1$ and $M^2$ metal. Exemplary embodiments include $Co^{3+}$ and/or $Fe^{3+}$.

Suitable anions A include, but are not limited to, halides such as chloride, bromide and iodide, nitrate, sulfate, carbonate, cyanide, oxalate, thiocyanate, isocyanate, perchlorate, isothiocyanate, an alkanesulfonate such as methanesulfonate, an arylenesulfonate such as p-toluenesulfonate, trifluoromethanesulfonate (triflate), and a $C_{1-4}$ carboxylate. Exemplary embodiments include the chloride ion.

Referring to Formula (I), r is an integer that is 4, 5 or 6. In exemplary embodiments, r is 4 or 6. Further, t is an integer from 0 to 2, and in exemplary embodiments t is 0. The sum of r+t may equal six.

In exemplary embodiments, the DMC catalyst is a zinc hexacyanocobaltate catalyst complex. The DMC catalyst may be complexed with t-butanol. The DMC catalyst used in exemplary embodiments may be a blend catalyst that includes of one or more DMC catalysts. The blend catalyst may optionally include a non-DMC catalyst, in which the DMC catalysts account for at least 75 wt % of the total weight of the blend catalyst. The blend catalyst may exclude any of Lewis acid catalyst that is added at a later time in the dual catalyst system.

Monomers

The monomers used to provide the polyether polyol include at least one selected from propylene oxide (1,2-propene oxide) and butylene oxide (1,2-butene oxide). The monomers may additionally include other monomers, such as the alkylene oxide monomers having at least three carbon atoms that are selected from 1,2-alkene oxide monomers having from three to ten carbon atoms (linear or branched) and/or arylalkylene oxide monomers. Exemplary other monomers include pentylene oxide (also known as 1,2-epoxypentane), hexylene oxide (also known as 1,2-epoxyhexane), octylene oxide (also known as 1,2-epoxyoctane), nonylene oxide (also known as 1,2-epoxynonane), decylene oxide (also known as 1,2-epoxydecane), isobutylene oxide, 4-methyl-1-pentylene oxide, and styrene oxide.

Use of the Catalyst Component

In embodiments where the one or more Lewis acid catalysts are used in the alkoxylation process of low hydroxyl equivalent weight starter compounds, also referred to as initiators, the process may proceed directly from the starter compound to a finished polyether polyol by the polymerization of one or more alkylene oxides. Further, the use of the Lewis acid catalyst during the polymerization reaction may reduce certain side reactions that lead to increased polydispersity and/or to increased acetal content in a final product.

The starter compound, also referred to as an initiator, has a low molecular weight and a nominal hydroxyl functionality of at least 2. The initiator is any organic compound that is to be alkoxylated in the polymerization reaction. The initiator may contain as many as 12 or more hydroxyl groups. For example, the initiator may be a diol, triol or hexol. Mixtures of starter compounds/initiators may be used. The initiator will have a hydroxyl equivalent weight less than that of the polyether product, e.g., may have a hydroxyl equivalent weight of less than 3500 g/mol equivalence, less than 333 g/mol equivalence, less than 300 g/mol equivalence, greater than 30 g/mol equivalence, from 30 to 300 g/mol equivalence, from 30 to 250 g/mol equivalence, from 50 to 250 g/mol equivalence, etc. Exemplary, initiator compounds include, but are not limited to, ethylene glycol, diethylene glycol, triethylene glycol, propylene glycol, dipropylene glycol, tripropylene glycol, 1,4-butanediol, 1,6-hexanediol, 1,8-octanediol, cyclohexane dimethanol, glycerin, trimethylolpropane, trimethylolethane, pentaerythritol, sorbitol, sucrose, and/or alkoxylates (especially ethoxylates and/or propoxylates) any of these that have a number average molecular weight less than that of the product of the polymerization (e.g., less than 5000 g/mol, less than 4000 g/mol, less than 3000 g/mol, less than 2000 g/mol, and/or less than 1000 g/mol).

The starter compound/initiator may be a low molecular weight polyether polyol that has been formed using an alkylene oxide such as propylene oxide, ethylene oxide, and/or butylene oxide (e.g., which is polymerized with another starter compound/initiator). The starter compound may be a diol or triol. For example, the starter compound is an all-propylene oxide-based diol or triol. The starter compound may have a hydroxyl functional based equivalent weight of may have a hydroxyl equivalent weight of less than 3500 g/mol equivalence, less than 333 g/mol equivalence, less than 300 g/mol equivalence, greater than 30 g/mol equivalence, from 30 to 300 g/mol equivalence, from 30 to 250 g/mol equivalence, from 50 to 250 g/mol equivalence, etc.

When the Lewis acid catalyst is used, the temperature of the reactor may be reduced at least 20° C. as compared to when the DMC catalyst is used. For example, the temperature for use of a DMC catalyst may be from 125° C. to 160° C. (e.g., during a time at which a propylene oxide feed is gradually/slowly added to the reactor and after the time at which the starter compound is mixed with the DMC catalyst). The temperature for use of the Lewis acid catalyst may be from 25° C. to 115° C. and/or from 60° C. to 115° C. In exemplary embodiments, the control of the relative contribution of a mixture containing an active DMC catalyst and an active Lewis acid may enable the Lewis acid to dominate the addition of oxirane onto chain ends.

In an exemplary embodiment, when the polyether polyol is derived from propylene oxide-based initiator (e.g., a polyoxypropylene starter compound), during the polymerization process propylene oxide and/or butylene oxide may be added to the reaction mixture to form the polyether polyol having a number average molecular weight greater than the number average molecular weight of the initiator. For example, the polyether polyol may have a molecular weight of at least 250 g/mol, at least 1000 g/mol, at least 2000 g/mol, at least 3000 g/mol, at least 5000 g/mol, at least 6000 g/mol, and/or at least greater than 100 g/mol.

The polymerization reaction can be performed in any type of vessel that is suitable for the pressures and temperatures encountered. In a continuous or semi-continuous process the vessel may have one or more inlets through which the alkylene oxide and additional initiator compound may be introduced during the reaction. In a continuous process, the reactor vessel should contain at least one outlet through which a portion of the partially polymerized reaction mixture may be withdrawn. A tubular reactor that has single or multiple points for injecting the starting materials, a loop reactor, and a continuous stirred tank reactor (CSTR) are all suitable types of vessels for continuous or semi-continuous operations. An exemplary process is discussed in U.S. Patent Publication No. 2011/0105802.

The resultant polyether polyol product may be further treated, e.g., in a flashing process and/or stripping process. For example, the polyether polyol may be treated to reduce catalyst residues even though some catalyst residue may be retained in the product. Moisture may be removed by stripping the polyol. The polyether polyol derived from propylene oxide, according to embodiments, may have a Lewis acid catalyst concentration (in ppm in the final polyoxypropylene polyol) of from 50 ppm to 1000 ppm (e.g., 100 ppm to 500 ppm and/or 100 ppm to 250 ppm).

The polymerization reaction may be characterized by the "build ratio", which is defined as the ratio of the number average molecular weight of the polyether product to that of the initiator compound. This build ratio may be as high as 160, but is more commonly in the range of from 2.5 to about 65 and still more commonly in the range of from 2.5 to about 50. The build ratio is typically in the range of from about 2.5 to about 15, or from about 7 to about 11 when the polyether product has a hydroxyl equivalent weight of from 85 to 400.

Exemplary embodiments relate to preparing the polyether polyols using one or more of certain Lewis acid catalysts as polymerization catalysts that may achieve low acetal content in the resultant polyether polyols (e.g., less than 2.0 mol %, less than 1.5 mol %, less than 1.0 mol %, less than 0.8 mol %, less than 0.5 mol %, less than 0.4 mol %, less than 0.3 mol %, less than 0.2 mol %, less than 0.1 mol %, etc.), based on the total moles of carbon in the resultant polyol chains, while still receiving high molecular weight polyols (e.g., polypropylene oxide polyols, poly-propylene oxide/butylene oxide polyols, polybutylene oxide polyols, etc.)

Exemplary embodiments relate to using one or more of certain Lewis acid catalyst as polymerization catalyst, such that use of the Lewis acid catalyst may result in higher activation barriers to aldehyde formation, which is an undesired product, as compared to the activation barrier for forming the desired polyether polyol product or intermediate. As such the formation of the desired product or intermediate product may be favored during the polymerization process compared to the undesired products. For example, the activation barrier to aldehyde formation may be greater than 5.0 kcal/mol, greater than 7.0 kcal/mol, greater than 8.0 kcal/mol, and/or greater than 9.0 kcal/mol. The activation barrier to aldehyde formation may be less than 30 kcal/mol and/or less than 20 kcal/mol.

Polyether polyols produced in accordance with embodiments may be useful for making polyurethanes. The polyurethane polymers may be prepared as the reaction product of the polyether polyol and an isocyanate (such as a polyisocyanate, of which examples include methylenediphenyl diisocyanate also known as MDI and toluene diisocyanate also known as TDI). For example, higher equivalent weight polyether polyol products may be useful in making elastomeric or semi-elastomeric polyurethane products, including noncellular or microcellular elastomers, coatings, adhesives, sealants, composites, and flexible, rigid, and viscoelastic polyurethane foams. The polyurethane foams may be made in a slabstock or molding process.

All parts and percentages are by weight unless otherwise indicated. All molecular weight values are based on number average molecular weight unless otherwise indicated.

Examples

Approximate properties, characters, parameters, etc., are provided below with respect to various working examples, comparative examples, and the materials used in the working and comparative examples.

Catalyst Synthesis

The general production for catalyst synthesis is as follows. Unless otherwise noted, all experimental procedures and manipulations of chemical substances are performed in a nitrogen-purged glove box or on a Schlenk line. All bulk reaction solvents (toluene, diethyl ether, hexane, tetrahydrofuran (THF)) are dried by passage through columns of alumina and Q5 reactive scavenger. All other solvents are purchased from Aldrich anhydrous grade and stored over activated 3 Å molecular sieves prior to use. NMR solvents ($CDCl_3$ and $C_6D_6$), obtained from Cambridge Isotope Laboratories, Inc., are dried over molecular sieves or, in the case of $C_6D_6$, dried using Na/K alloy. Further, 1-bromo-3,5-bis(trifluoromethyl)benzene, 1-bromo-2,4-difluoro-3-trifluoromethylbenzene, and 1-bromo-3,5-difluoro-4-trimethylbenzene are purchased from Oakwood Chemical. Also, 1-bromo-2,4,6-trifluoro-3-trifluoromethylbenzene, isopropylmagnesium chloride-lithium chloride (solution in THF), and boron trifluoride diethyletherate) are obtained from Sigma-Aldrich and used as received. Further, isopropylmagnesium chloride lithium chloride complex (solution in THF) is titrated before use using 1.00 M decanol in toluene with 1,10-phenanthroline as an indicator.

Multinuclear NMR spectra ($^1H$, $^{13}C$, $^{19}F$) are collected on one of the following instruments: Varian MR-400 or Varian VNMRS-500. The $^1H$ and $^{13}C$ NMR chemical shifts are referenced in parts per million relative to residual solvent peaks: $^1H$—7.15 ppm for $C_6D_6$, 7.25 ppm for $CDCl_3$; $^{13}C$—128.00 ppm for $C_6D_6$, and 77.00 ppm for $CDCl_3$. Boron-11 NMR chemical shifts are referenced externally to $BF_3(Et_2O)$ (0 ppm), and $^{19}F$ NMR chemical shifts are referenced externally to $CFCl_3$ (0 ppm). Sub-ambient reaction temperatures, except when dry ice or ice were the sole means of cooling, are measured using an Extech Instruments EasyView™10 Dual K model EA 10 thermometer with a fine JKEM sensor PTFE wire K 36INJ.

Catalyst 1 is tris(3,5-bis(trifluoromethyl)phenyl)borane.

Catalyst 2, is the THF adduct of Catalyst 1.

Catalyst 1 and 2 are prepared according to the following Schematic 2:

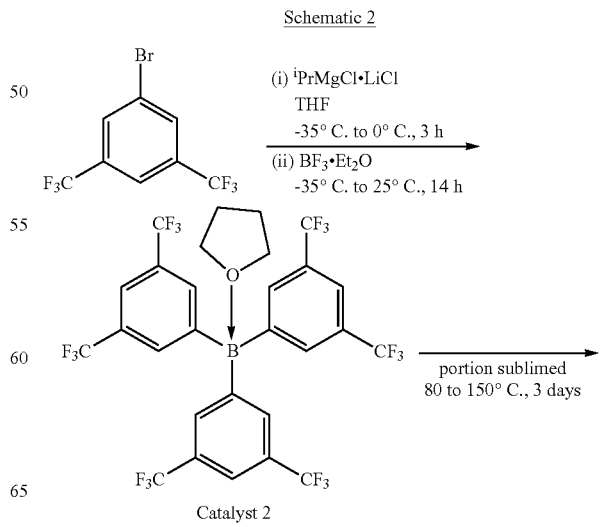

Schematic 2

Catalyst 2

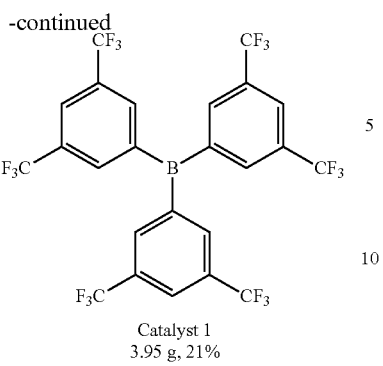

Catalyst 1
3.95 g, 21%

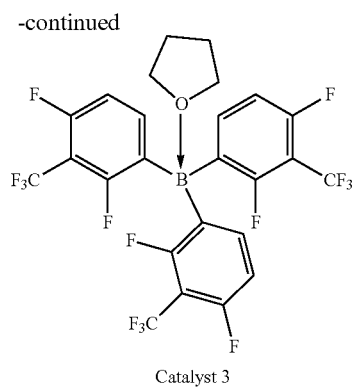

Catalyst 3

In particular, isopropylmagnesium chloride-lithium chloride (70.8 mL, 87.0 mmol, 1.23 M solution in THF) is added to a solution of 1-bromo-3,5-bis(trifluoromethyl)benzene (25.5 g, 87.0 mmol) in THF (250 mL) which is in an acetone bath cooled with dry ice and held within a temperature range of between −35° C. to −25° C. during the addition. After the addition is complete, the reaction flask is transferred to an ice bath (0° C.) and the reaction mixture is stirred for 3 hours. The reaction mixture is cooled to about −35° C. and boron trifluoride diethyletherate (4.26 mL, 29.0 mmol) is added while maintaining the reaction mixture at a temperature range of between −35° C. to −25° C. The reaction mixture is allowed to warm to room temperature while it is stirred overnight. The resultant $^{19}$F NMR spectra of the reaction mixture shows a major peak (95%) at δ−63.2 and a minor peak (5%) at δ−63.7 corresponding to 1-bromo-3,5-bis(trifluoromethyl)benzene. Next, the THF is removed from the reaction mixture under reduced pressure. The residue is extracted with toluene and filtered using several PTFE-frits because the very fine precipitate may be difficult to filter. The volatiles are removed under reduced pressure to give a very viscous oil. A portion of the product (about ⅔ to ¾) is put in a sublimator and sublimed (by starting at 80° C. and gradually increasing the temperature to 150° C. over several days in an oil bath under ≤1 mtorr vacuum) to give 3.95 grams (6.07 mmol, 21%) of white solid on the sublimator finger. Small crystals may also be present. This material is characterized by multinuclear NMR spectroscopy as Catalyst 1. Additional, less pure, product is scraped out of the top portion of the sublimator body, in an amount of 2.01 grams. The less pure material, which by NMR is characterized as a 2:1 mixture of borane to THF, is dissolved in THF, filtered, and the volatiles are removed under reduced pressure. This material is characterized by multinuclear NMR spectroscopy as Catalyst 2 (2.00 g, 2.77 mmol, 9.5%) Total yield: 6.07 mmol Catalyst 1 and 2.77 mmol Catalyst 2 (30% overall yield).

Catalyst 3 is the THF adduct of tris(2,4-difluoro-3-(trifluoromethyl)phenyl)borane and is prepared according to Schematic 3:

Schematic 3

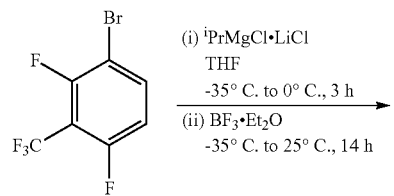

(i) $^i$PrMgCl•LiCl
THF
−35° C. to 0° C., 3 h
(ii) BF$_3$•Et$_2$O
−35° C. to 25° C., 14 h

In particular, isopropylmagnesium chloride-lithium chloride (15.6 mL, 19.2 mmol, 1.23 M solution in THF) is added to a solution of 1-bromo-2,4-difluoro-3-trifluoromethylbenzene (5.00 g, 19.2 mmol) in THF (100 mL) which is in an acetone bath cooled with dry ice and held within a temperature range of between −35° C. to −25° C. during the addition. After the addition is complete, the reaction flask is transferred to an ice bath (0° C.) and the reaction mixture is stirred for 3 hours. The reaction mixture is cooled to about −35° C. and boron trifluoride diethyletherate (0.79 mL, 6.4 mmol) is added while maintaining the reaction mixture at a temperature range of between −35° C. to −25° C. The reaction mixture is allowed to warm to room temperature while it is stirred overnight. Next, the THF is removed from the reaction mixture under reduced pressure. The residue is extracted with toluene and filtered using a PTFE frit. The volatiles are removed from the filtrate under reduced pressure to give the product, the THF adduct of tris(2,4-difluoro-3-(trifluoromethyl)phenyl)borane.

Catalyst 4 is the THF adduct of tris(3,5-difluoro-4-(trifluoromethyl)phenyl)borane and is prepared according to Schematic 4:

Schematic 4

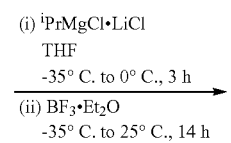

(i) $^i$PrMgCl•LiCl
THF
−35° C. to 0° C., 3 h
(ii) BF$_3$•Et$_2$O
−35° C. to 25° C., 14 h

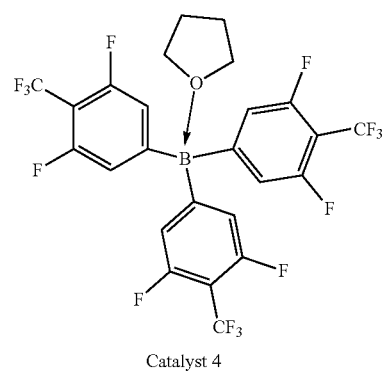

Catalyst 4

In particular, isopropylmagnesium chloride-lithium chloride (31.1 mL, 38.3 mmol, 1.23 M solution in THF) is added to a solution of 1-bromo-3,5-difluoro-4-trifluoromethylbenzene (10.0 g, 38.3 mmol) in THF (150 mL) which is in an acetone bath cooled with dry ice and held within a temperature range of between −35° C. to −25° C. during the addition. After the addition is complete, the reaction flask is transferred to an ice bath (0° C.) and the reaction mixture is stirred for 3 hours. The reaction mixture is cooled to about −35° C. and boron trifluoride diethyletherate (1.58 mL, 12.8 mmol) is added while maintaining the reaction mixture at a temperature range of between −35° C. to −25° C. The reaction mixture is allowed to warm to room temperature while it is stirred overnight. Next, the THF is removed from the reaction mixture under reduced pressure. The residue is extracted with toluene and filtered using a PTFE frit. The volatiles are removed from the filtrate under reduced pressure to give the product, the THF adduct of tris(3,5-difluoro-4-(trifluoromethyl)phenyl)borane.

Catalyst 5 is the THF adduct of tris(2,4,6-trifluoro-3-(trifluoromethyl)phenyl)borane and is prepared according to Schematic 5:

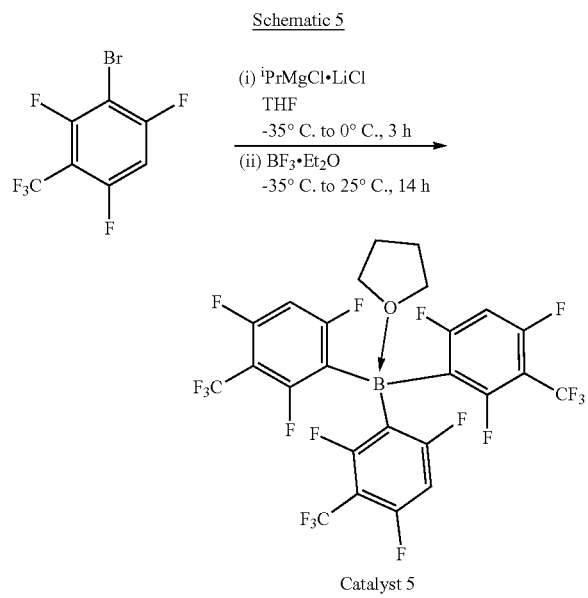

Catalyst 5

In particular, isopropylmagnesium chloride-lithium chloride (5.9 mL, 7.3 mmol, 1.23 M solution in THF) is added to a solution of 1-bromo-2,4,6-trifluoro-3-trifluoromethylbenzene (2.00 g, 7.17 mmol) in THF (50 mL) which is in an acetone bath cooled with dry ice and held within a temperature range of between −35° C. to −25° C. during the addition. After the addition is complete, the reaction flask is transferred to an ice bath (0° C.) and the reaction mixture is stirred for 3 hours. The reaction mixture is cooled to about −35° C. and boron trifluoride diethyletherate (0.30 mL, 2.4 mmol) is added while maintaining the reaction mixture at a temperature range of between −35° C. to −25° C. The reaction mixture is allowed to warm to room temperature while it is stirred overnight. Next, the THF is removed from the reaction mixture under reduced pressure. The residue is extracted with toluene and filtered using a PTFE frit. The volatiles are removed from the filtrate under reduced pressure to give the product, the THF adduct of tris(2,4,6-trifluoro-3-(trifluoromethyl)phenyl)borane.

Catalyst A is tris(pentafluorophenyl)borane, also referred to as FAB (available from Boulder Scientific).

Catalyst B is a zinc hexacyanocobaltate catalyst complex (available from Covestro under the name Arcol 3® Catalyst).

Preparation of Polyols

For preparing the polyols, the following materials are principally used:

| | |
|---|---|
| P390 | A starter compound that is a polyoxypropylene diol having a number average molecular weight of approximately 390 g/mol (available from The Dow Chemical Company as VORANOL ™ P 390). |
| Glycerol | A polyol that contains three hydroxyl groups (available from Sigma-Aldrich Corporation) |
| V2070 | A polyoxypropylene triol having a number average molecular weight of approximately 700 g/mol, i.e., a low molecular weight PO triol (available from The Dow Chemical Company as VORANOL ™ 2070). |
| Solvent | A glycol diether that has no hydroxyl functionality (available from The Dow Chemical Company as PROGLYDE ™ DMM). |
| Additive | An acidifying agent that includes phosphoric acid. |

In particular, the following reaction may be carried out in a continuous flow reactor using Catalysts 1 to 5 as discussed above. The reactions may be carried out a manner as shown below in exemplary Schematic 6, and in view of the conditions provided in Table 1:

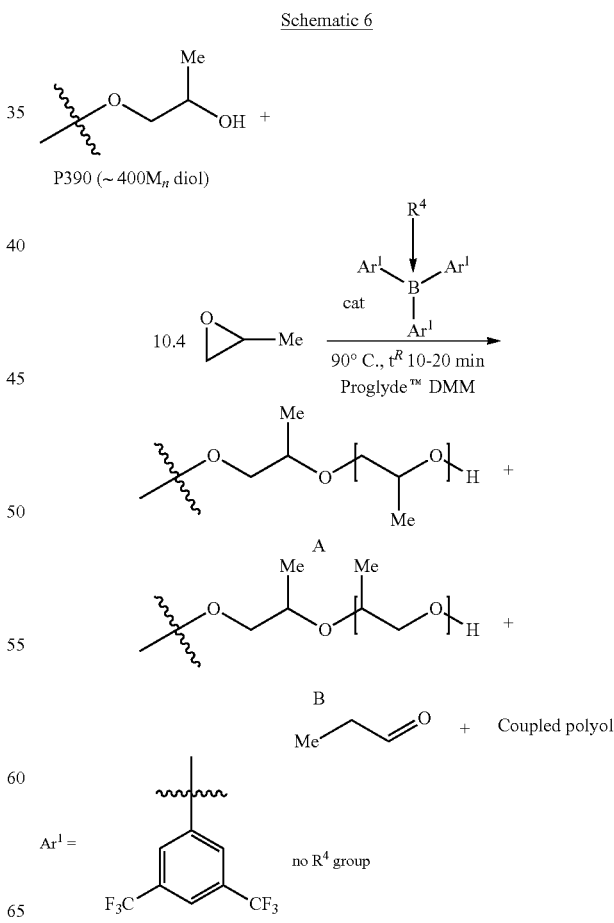

-continued

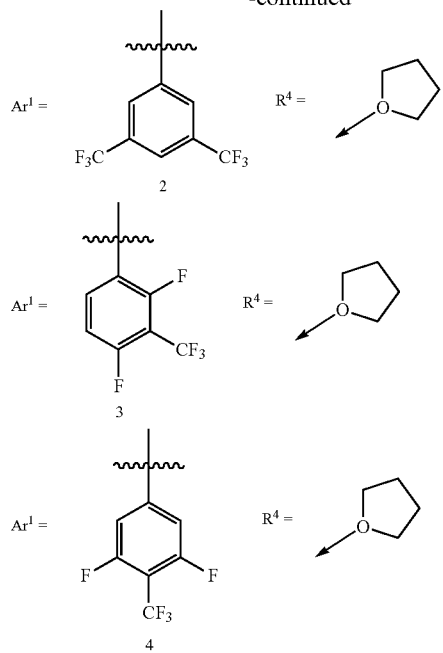

The polyols of Working Examples 1 to 5 and Comparative Examples A, B and C may be prepared using P390 as the initiator, propylene oxide (PO) as the monomer, and the Solvent according to the conditions outlined in Table 1, below. Referring to Table 1, the number average molecular weight (Mn) and polydispersity index (PDI) are determined according to the analytical methods discussed below. Referring to Tables 1 and 2, the PO binding enthalpy and activation barrier to aldehyde are determined according to the computational methods discussed below.

TABLE 1

| | Catalyst | Catalyst Con. (ppm) | Time (Min) | Temp (° C.) | $M_n$ | PDI | PO binding enthalpy (kcal/mol) | Activation barrier to aldehyde (kcal/mol) |
|---|---|---|---|---|---|---|---|---|
| Ex. A | — | — | 10 | 90 | 456 | 1.06 | n/a | n/a |
| Ex. B | A | 1000 | 10 | 90 | 955 ± 58 | 1.13 ± 0.01 | −7.2 | 4.8 |
| Ex. C | | | 20 | | 971 | 1.14 | | |
| Ex. 1 | 1 | 1000 | 10 | 90 | 848 | 1.09 | −5.7 | 9.1 |
| Ex. 2 | | | 20 | | 952 | 1.08 | | |
| Ex. 3 | 2 | 1000 | 10 | 90 | 901 | 1.09 | | |

TABLE 2

| | Catalyst | PO binding enthalpy (kcal/mol) | Activation barrier to aldehyde (kcal/mol) |
|---|---|---|---|
| Ex. 4 | 3 | −6.5 | 5.3 |
| Ex. 5 | 4 | −8.0 | 9.0 |

Comparative Example A is a negative control run without catalyst. This example is carried out by mixing the initiator and propylene oxide in the tubular reactor at 90° C. for 10 min. The products are stripped of volatile products using a nitrogen sparge followed by vacuum (42 mbar for 15 min) and analyzed by MALDI spectrometry. The measured Mn was similar to the Mn of the initiator indicating that any background, uncatalyzed reaction under these conditions is negligible.

The polyol samples for Working Examples 1 to 5 and Comparative Examples B and C, may be prepared in a continuous flow reactor that is a microreactor available from Vapourtec Inc. For the examples, neat PO monomer is fed to a pump via a pressure cylinder at 50 psig. A solvent reservoir containing the Solvent is connected to another pump. A 2-mL injection loop is utilized to introduce a solution of the specified catalyst and initiator (as 60 wt % of P390 in dipropylene glycol dimethyl ether) into the system. By controlling the flow rate, the catalyst and starter may introduced into the flow system at a defined rate. The PO monomer and initiator-catalyst-Solvent solution are combined at a mixing unit and fed into a 2-mL stainless steel coiled reactor. A back-pressure regulator set at 250 psig is used to control the system pressure and assist the PO to remain in a liquid phase. The continuous pressure reactor is charged with 0.1 mL/min of the initiator-catalyst-Solvent mixture. The propylene oxide is fed to the reactor at a constant feed rate of 0.1 mL/min. Once the initiator-catalyst-Solvent mixture is introduced into the sample loop, the first 5.13 mL of the product mixture is diverted to a scrubber consisting of 3 wt % aqueous potassium hydroxide. The next 3.04 mL of product mixture is collected and analyzed by MALDI spectrometry.

The Temperature in Table 1 is the temperature in the reactor. The Time is residence time, which is defined as follows:

$$\text{residence time} = \frac{\text{reactor volume}}{(\text{flow rate of pump } A + \text{flow rate of pump } B)}$$

When the flow rates of pumps A and B are each 0.1 mL/min, $$\text{residence time} = \frac{2 \text{ mL}}{(0.1 + 0.1) \text{ mL/min}} = 10 \text{ min}$$

When the flow rates of pumps A and B are each 0.05 mL/min, $$\text{residence time} = \frac{2 \text{ mL}}{(0.05 + 0.05) \text{ mL/min}} = 20 \text{ min}$$

The PDI is defined as the ratio of the weight-average molecular weight (Mw) to the number-average molecular weight (Mn). The PDI may represent a measure of the extent of acetal coupling, as this reaction may effectively double the molecular weight. Accordingly, a comparison of the PDI at similar Mn values may provide a measure of the selectivity of a catalyst for alkoxylation (intended reaction) versus isomerization of propylene oxide to propionaldehyde and subsequent acetalization. Lower PDI may be preferable for higher chemoselectivity.

The PO binding enthalpy is calculated relative to a resting state consisting of the free catalyst (where $R^4$ is not present) and PO. Favorable binding (higher negative values, for example greater than −5.5 kcal/mol, greater than −6.5 kcal/mol, etc) is preferable for higher activity. Referring to Tables 1 and 2, it is seen that the calculations on Catalysts 1 to 4 provide a favorable PO binding enthalpy such that favorable activity is realized. Another measure of activity is the ring-opening barrier shown below. Lower ring-opening barriers are preferable for higher activity.

The activation barrier to aldehydes determines the amount of aldehyde and acetal formed, as shown below. Higher activation barriers are preferable for lower aldehyde and subsequent acetal formation.

Referring to Working Examples 1 to 5 and Comparative Examples B and C, it is found that the activation barrier to aldehydes and acetals is significantly higher for Catalysts 1 to 4 compared to Catalyst A. As such, it is unexpectedly found that the structures of Catalysts 1 to 4 may allow for strongly disfavoring aldehyde and acetal formation, as compared to Catalyst A.

Additional, Working Examples 6 to 9 and Comparative Example D, E and F are carried out in a semi-batch process using varying initiators and monomers, using the Catalysts 2 and A, and in view of conditions provided in Tables 3 to 6 and according to Schematic 7:

Schematic 7

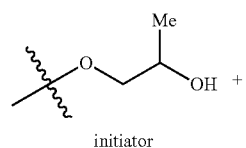

initiator

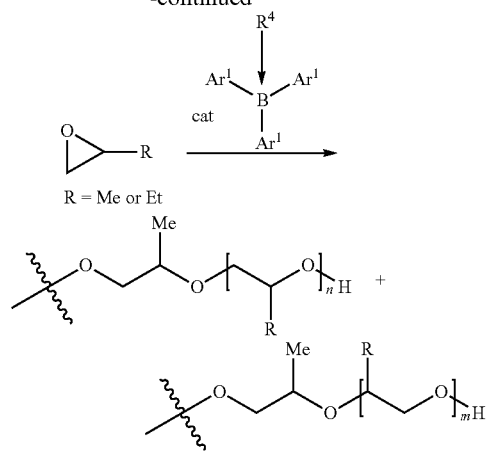

Referring to Tables 3 to 6, Init refers to the initiator used, Mon refers to the monomer used, and M/I refers to the ratio of the monomer to initiator used. The monomer used may be propylene oxide (PO).

TABLE 3

| Init | Mon | M/I ratio | Catalyst | Catalyst Con. (ppm) | Temp (° C.) | Mn | PDI | Acetal Content (mol %) |
|---|---|---|---|---|---|---|---|---|
| Ex. D | P390 | PO | 27.5 | A | 250 | 55 | 2246 | 1.16 | 1.52 |
| Ex. 6 | P390 | PO | 27.5 | 2 | 250 | 55 | 2060 | 1.08 | 0.52 |

TABLE 4

| Init | Mon | M/I | Cat. | Cat. Con. (ppm) | Temp (° C.) | $M_n$ | PDI | Acetal (mol %) |
|---|---|---|---|---|---|---|---|---|
| Ex. E | P390 | PO | 10 | A | 1000 | 90 | 1295 | 1.13 | 1.50 |
| Ex. 7 | P390 | PO | 10 | 1 | 1000 | 90 | 1269 | 1.05 | 0.20 |

TABLE 5

| Init | Mon | M/I ratio | Catalyst | Catalyst Con. (ppm) | Temp (° C.) | Mn | PDI | Acetal Content (mol %) |
|---|---|---|---|---|---|---|---|---|
| Ex. F | P390 | PO | 10 | A | 250 | 90 | 1027 | 1.14 | 0.83 |
| Ex. 8 | P390 | PO | 10 | 2 | 250 | 90 | 983 | 1.05 | 0.2 |

TABLE 6

| Init | Mon | M/I | Cat. | Cat. Con. (ppm) | Temp (° C.) | $M_n$ | PDI | Acetal (mol %) |
|---|---|---|---|---|---|---|---|---|
| Ex. 9 | Glycerol | PO | 6.2 | 2 | 250 | 80 | 386 | 1.17 | 0.9 |

For the semi-batch alkoxylation reactions, the initiator is dried and charged into the pressure reactor using one of three procedures.

Procedure A: A stainless steel cylinder is dried in the oven at 125° C. for 6 hours. The cylinder is cooled under a stream of nitrogen. The empty Parr reactor is dried at 140° C. jacket temperature under a nitrogen purge for 1 hours. The initiator is dried in glassware at 110° C. for 2 hours under a vacuum of 65 mbar and then transferred to the stainless steel cylinder under vacuum. The cylinder is weighed and its contents are transferred to the Parr reactor using nitrogen pressure. The cylinder is weighed after transfer to determine the amount charged to the Parr reactor.

Procedure B: The initiator is charged directly to the Parr reactor via a funnel. Drying is performed in the reactor for 120 min at 120° C. under a nitrogen purge.

Procedure C: The initiator is charged directly to the Parr reactor via a funnel. Drying is performed in the reactor for 180 min at 140° C. under a nitrogen purge.

Comparative Example D (Table 3): A 600 mL pressure reactor is charged with 59.3 grams of VORANOL™ P390, a poly(propylene oxide) diol of number-average molecular weight 400, using Procedure A. A solution of catalyst A (74 mg) in anhydrous tetrahydrofuran (2 mL) is added in one portion through a sample addition port under a nitrogen purge. After purging for 5 min, the nitrogen purge is stopped and the reactor vent is closed. Propylene oxide (237.3 g) is added to the reactor at a reaction temperature of 55° C. and a constant feed rate of 1.25 g/min. Upon completion of propylene oxide feed, the reaction is allowed to digest for 20 min at 55° C. The reaction mixture is vented and heated to 90° C. under a nitrogen purge. The reaction mixture is purged at 90° C. for 30 minutes, cooled to 60° C., and the product is collected (265.2 g, 89%). Number-average molecular weight=2246 (by gel permeation chromatography); Polydispersity index (PDI)=1.16 (by gel permeation chromatography); acetals=1.52 mol % (by inverse-gated $^{13}$C NMR spectroscopy).

Working Example 6 (Table 3): A 600 mL pressure reactor is charged with 60.7 grams of VORANOL™ P390, a poly(propylene oxide) diol of number-average molecular weight 400, using Procedure C. A solution of Catalyst 2 (76 mg) in anhydrous tetrahydrofuran (2 mL) is added in one portion through a sample addition port under a nitrogen purge. After purging for 5 min, the nitrogen purge is stopped and the reactor vent is closed. Propylene oxide (294.9 mL) is added to the reactor at a reaction temperature of 55° C. and a constant feed rate of 1.5 mL/min. Upon completion of propylene oxide feed, the reaction is allowed to digest for 25 min at 55° C. The reaction mixture is vented and heated to 90° C. under a nitrogen purge. The reaction mixture is purged at 90° C. for 30 minutes, cooled to 60° C., and the product is collected (292.4 g, 98%). Number-average molecular weight=2060 (by gel permeation chromatography); Polydispersity index (PDI)=1.08 (by gel permeation chromatography); acetals=0.52 mol % (by inverse-gated $^{13}$C NMR spectroscopy).

Comparative Example E (Table 4): A 500 mL pressure reactor was charged with 51 grams of VORANOL™ P400, a poly(propylene oxide) diol of number-average molecular weight 440. The reactor was heated to 110° C. for 2 h under a purge of nitrogen through the liquid phase in order to dry the initiator. The reactor was cooled to 60° C. and catalyst A (125 mg) was added in one portion to the reactor shell. The reactor shell was clamped to the head and heated to 90° C. under a nitrogen purge. When the temperature of the initiator/catalyst mixture had reached 90° C., the nitrogen and vent valves were closed. Propylene oxide (90 mL) was added to the reactor at a constant feed rate of 0.6 mL/min. Upon completion of propylene oxide feed, the reaction was allowed to digest for 30 min at 90° C. and cooled to 50° C. under nitrogen purge. After purging at 50° C. for 10 minutes the product was collected (124 g, 99%). Number-average molecular weight=1259 (by gel permeation chromatography); Polydispersity index (PDI)=1.19 (by gel permeation chromatography); acetals=1.5 mol (by inverse-gated $^{13}$C NMR spectroscopy).

Working Example 7 (Table 4): A 500 mL pressure reactor was charged with 51 grams of VORANOL™ P400, a poly(propylene oxide) diol of number-average molecular weight 440. The reactor was heated to 110° C. for 2 h under a purge of nitrogen through the liquid phase in order to dry the initiator. The reactor was cooled to 60° C. and catalyst 1 (125 mg) was added in one portion to the reactor shell. The reactor shell was clamped to the head and heated to 90° C. under a nitrogen purge. When the temperature of the initiator/catalyst mixture had reached 90° C., the nitrogen and vent valves were closed. Propylene oxide (119 mL) was added to the reactor at a constant feed rate of 0.6 mL/min. Upon completion of propylene oxide feed, the reaction was allowed to digest for 30 min at 90° C. and cooled to 50° C. under nitrogen purge. After purging at 50° C. for 10 minutes the product was collected (143 g, 96%). Number-average molecular weight=1286 (by gel permeation chromatography); Polydispersity index (PDI)=1.07 (by gel permeation chromatography); acetals=0.2 mol % (by inverse-gated $^{13}$C NMR spectroscopy).

Comparative Example F (Table 5): A 600 mL pressure reactor is charged with 61.2 grams of VORANOL™ P390, a poly(propylene oxide) diol of number-average molecular weight 400, using Procedure B. A solution of Catalyst A (38 mg) in anhydrous tetrahydrofuran (2 mL) is added in one portion through a sample addition port under a nitrogen purge. After purging for 5 min, the nitrogen purge is stopped and the reactor vent is closed. Propylene oxide (89.1 g) is added to the reactor at a reaction temperature of 90° C. and a constant feed rate of 0.75 g/min. Upon completion of propylene oxide feed, the reaction is allowed to digest for 20 min. The reaction mixture is vented and purged with nitrogen at 90° C. for 30 minutes, cooled to 60° C., and the product is collected (141.7 g, 95%). Number-average molecular weight=1027 (by gel permeation chromatography); Polydispersity index (PDI)=1.14 (by gel permeation chromatography); acetals=0.83 mol % (by inverse-gated $^{13}$C NMR spectroscopy).

Working Example 8 (Table 5): A 600 mL pressure reactor is charged with 59.5 grams of VORANOL™ P390, a poly(propylene oxide) diol of number-average molecular weight 400, using Procedure B. A solution of Catalyst 2 (36 mg) in anhydrous tetrahydrofuran (2 mL) is added in one portion through a sample addition port under a nitrogen purge. After purging for 5 min, the nitrogen purge is stopped and the reactor vent is closed. Propylene oxide (86.7 g) is added to the reactor at a reaction temperature of 90° C. and a constant feed rate of 0.75 g/min. Upon completion of propylene oxide feed, the reaction is allowed to digest for 32 min. The reaction mixture is vented and purged with nitrogen at 90° C. for 30 minutes, cooled to 60° C., and the product is collected (138.4 g, 95%). Number-average molecular weight=983 (by gel permeation chromatography); Polydispersity index (PDI)=1.05 (by gel permeation chromatography); acetals=0.2 mol % (by inverse-gated $^{13}$C NMR spectroscopy).

Working Example 9 (Table 6): A 500 mL pressure reactor is charged with 62 grams of Glycerol, using Procedure C. A solution of Catalyst 2 (76 mg) in anhydrous tetrahydrofuran (2 mL) is added in one portion through a sample addition port under a nitrogen purge. After purging for 5 min, the nitrogen purge is stopped and the reactor vent is closed. Propylene oxide (292.6 mL) is added to the reactor at a reaction temperature of 80° C. and a constant feed rate of 1.5 mL/min. Upon completion of propylene oxide feed, the reaction is allowed to digest for 18 min. The reaction mixture is vented and purged with nitrogen at 80° C. for 30 minutes, cooled to 60° C., and the product is collected (281 g, 94%). Number-average molecular weight=386 (by gel permeation chromatography); Polydispersity index (PDI)=1.17 (by gel permeation chromatography); acetals=0.9 mol % (by inverse-gated $^{13}$C NMR spectroscopy).

For Working Examples 6 to 9 and Comparative Example D, E and F, the mol % of acetal in the resultant polyol samples is measured (based on the total moles of carbon in the resultant polyol chains). Referring to Tables 3 to 6, it is seen that the moles of acetal in the polyols is significantly lower when using Catalysts 1 and 2, as compared to Catalyst A.

A process for the preparation of a polyether polyol may be carried out in a continuous or semi-batch process using a sequential dual catalyst process, similar to International Publication No. WO 2016/064698, which is incorporated by reference.

Working Example 10: A 600 mL pressure reactor is charged with 60 grams of VORANOL™ P390, a poly(propylene oxide) diol of number-average molecular weight 400, using Procedure B. A solution of Catalyst 3 (36 mg) in anhydrous tetrahydrofuran (2 mL) is added in one portion through a sample addition port under a nitrogen purge. After purging for 5 min, the nitrogen purge is stopped and the reactor vent is closed. Propylene oxide (90 g) is added to the reactor at a reaction temperature of 90° C. and a constant feed rate of 0.75 g/min. Upon completion of propylene oxide feed, the reaction is allowed to digest for 30 min. The reaction mixture is vented and purged with nitrogen at 90° C. for 30 minutes, cooled to 60° C., and the product is collected.

Working Example 11: A 600 mL pressure reactor is charged with 60 grams of VORANOL™ P390, a poly(propylene oxide) diol of number-average molecular weight 400, using Procedure B. A solution of Catalyst 4 (36 mg) in anhydrous tetrahydrofuran (2 mL) is added in one portion through a sample addition port under a nitrogen purge. After purging for 5 min, the nitrogen purge is stopped and the reactor vent is closed. Propylene oxide (90 g) is added to the reactor at a reaction temperature of 90° C. and a constant feed rate of 0.75 g/min. Upon completion of propylene oxide feed, the reaction is allowed to digest for 30 min. The reaction mixture is vented and purged with nitrogen at 90° C. for 30 minutes, cooled to 60° C., and the product is collected.

Working Example 12: A 600 mL pressure reactor is charged with 60 grams of VORANOL™ P390, a poly(propylene oxide) diol of number-average molecular weight 400, using Procedure B. A solution of Catalyst 5 (36 mg) in anhydrous tetrahydrofuran (2 mL) is added in one portion through a sample addition port under a nitrogen purge. After purging for 5 min, the nitrogen purge is stopped and the reactor vent is closed. Propylene oxide (90 g) is added to the reactor at a reaction temperature of 90° C. and a constant feed rate of 0.75 g/min. Upon completion of propylene oxide feed, the reaction is allowed to digest for 30 min. The reaction mixture is vented and purged with nitrogen at 90° C. for 30 minutes, cooled to 60° C., and the product is collected.

The analytical methods used with respect to the examples are described below:

Determination of $M_n$ for semibatch products: Gel Permeation Chromatography (GPC) analysis is used for determination of number average molecular weight (Mn), which is carried out at a flow rate of 1.0 mL/min using four PLgel organic GPC columns connected in series (3 µm, Agilent Inc.) and tetrahydrofuran as eluent. The column temperature is 40° C. VORANOL™ CP 6001, VORANOL™ 210, 230-660, and 230-056N are used as standards.

Determination of $M_n$ and PDI for continuous products: Samples are analyzed using a Bruker UltrafleXtreme MALDI-TOF/TOF MS (Bruker Daltronics Inc., Billerica, Mass.) equipped with a 355-nm Nd:YAG laser. Spectra are obtained in the positive ion reflection mode with a mass resolution greater than 20,000 full-width at half-maximum height (fwhm); isotopic resolution was observed throughout the entire mass range detected; and the laser intensity was set approximately 10% greater than threshold. Instrument voltages are optimized for each spectrum to achieve the best signal-to-noise ratio. External mass calibration is performed using protein standards (Peptide Mix II) from a Peptide Mass Standard Kit (Bruker Daltronics) and a seven-point calibration method using Bradykinin (clip 1-7) (m=757.40 Da), Angiotensin II (m=1046.54 Da), Angiotensin I (m=1296.68 Da), Substance P (m=1347.74 Da), ACTH (clip 1-17) (m=2093.09 Da), ACTH (clip 18-39) (m=2465.20 Da), and Somatostatin 28 (m=3147.47 Da) to yield monoisotopic mass accuracy better than Δm=±0.05 Da. The m+1 peaks are used for positive ion mode and the m−1 peaks for negative ion mode. The instrument is calibrated before each measurement to ensure constant experimental conditions.

For CID fragmentation experiments, argon is used as a collision gas at pressures of $1.5 \times 10^{-6}$ Torr and the collision energy amounts to 20 keV. All spectra are acquired in the reflection mode with a mass resolution greater than 20,000 full-width at half-maximum height (fwhm); isotopic resolution is observed throughout the entire mass range detected. MALDI spectra are run in dithranol (Aldrich) matrix, optionally doped with sodium trifluoroacetate (NaTFA; Aldrich). Samples are prepared using the dried-droplet method. 5,6 Dithranol (20 mg/mL in THF), sodium trifluoroacetate (when used) (15 mg/mL in THF), and polymer (in THF) were mixed using the following ratios: 50 µL of Dithranol solution, 10 µL of polymer solution, 1.5 µL of NaTFA solution. After vortexing the mixture for 30 sec, 1 µL of the mixture is pipetted on the MALDI sample plate and allowed to air dry at room temperature. Spotting is performed using four replicates to ensure a good sampling of the mixture, and to account for variation in the MALDI sample deposition process. MALDI data is collected by slowly rastering the laser along the sample spot, with an average of 10,000 shots per spectrum. MS and MS/MS data are processed using Polymerix 3.0 software supplied by Sierra Analytics (Modesto, Calif.).

MALDI Data Analysis Using Polymerix software (Sierra Analytics): MALDI data is imported into Polymerix software for data analysis (Mn and PDI determination). The Polymerix software is used to calculate the relative percentages and Mn of each species series of interest. The first step is the construction of a template that identifies each species series of interest. This template should include the end groups of the PO repeat unit (58.04186 Da) and the cationization agent for each structure. For the sake of simplicity, when calculating the end groups for Polymerix, a hydrogen atom (1.0078 Da) is designated as the first terminal group and the remaining portion of the structure (minus the repeat unit) is designated at the second terminal group. With the template in place, the MALDI data can be imported, in the form of an ASCII file, and the Polymerix software will calculate the relative percentage for each species series along with the overall Mn and Mw of the sample. Note that due to the possibility of preferential desorption of low mass species, along with mass discrimination effects of the detector and the TOF-MS reflectron, the Mn calculation is generally more accurate than Mw.

Determination of acetal content by inverse-gated $^{13}$C NMR spectroscopy: Samples are prepared in 10-mm NMR tubes as ~90% solutions in DMSO-$d_6$ for $^{13}$C-NMR analysis to measure the level of acetal species. $^{13}$C NMR data is acquired using a Bruker Avance 400-MHz spectrometer equipped with a cryoprobe using at least 64 transient scans and a 30-second relaxation delay (optimized for quantitative measurements). The acquisition is carried out using spectral width of 25000 Hz for $^{13}$C and a file size of 65K data points. Relative moles of acetal species are measured by integrating the area under resonances from acetal carbons.

$$\text{mole \% acetal} = 100 \times \frac{\text{relative moles of acetal carbon}}{\text{sum of relative moles of all carbon species in the spectrum}}$$

The percentage coefficient of variation (100*standard deviation/mean) for the method is measured by preparing and analyzing one sample in triplicate and was found to be 10%.

Computational Methodology for determination of binding enthalpy and activation barrier to aldehyde: Computational Methodology: The structures of species in ground and transition states are optimized using Density Functional Theory (DFT) at B3LYP/6-31g** level. The effect of dielectric medium is included by using conductor like polarizable continuum model (CPCM), where diethylether (c=4.2) is used as the medium of choice. The vibrational analysis on the ground state geometries is performed and the lack of imaginary frequencies is used to ascertain the minima in the potential energy surface (PES). On the other hand, the same analysis on the transition state geometries indicated one imaginary frequency. In the latter case, the GaussView program is used to visualize the vibrational mode with imaginary frequency in order to ensure that the atoms moved along the desired reaction coordinate. For both ground-state and transition state geometries, the vibrational analysis is used to compute the enthalpy ($H_{298}$) at 298 K by augmenting zero point energy to the electronic energy. For both ground state and transition state, various conformations were explored and the enthalpy of the lowest conformation was used to calculate binding and the barrier height for aldehyde formation. These calculations were performed using G09 suit of programs.

Computational determination of free (or accessible) volume: Once the optimized geometry of free catalysts (where the catalyst is not bound to the optional $R^4$ Lewis base) or coordinated complexes (where a catalyst is bound to the optional $R^4$ Lewis base) are obtained using the above method, a sphere of radius 3.0 Å is placed around the B atom (the volume of this sphere is denoted as V1). This is followed by placing spheres on other atoms; the radii of these spheres are chosen to be the van der Waals radii of respective atoms. The volume of the sphere centered on B which is occluded by spheres on other atoms is computed using a Monte Carlo integration technique. The occluded volume is represented as V2. The free volume (FV) is calculated using the following equation:

$$FV = 1 - (V2/V1)$$

The FV descriptor varies between 0 and 1. This technique is implemented using Pipeline Pilot tool kit. This procedure is used in literature to understand bond dissociation trends.

The invention claimed is:

1. A method of producing a polyether polyol, comprising:
   reacting a low molecular weight initiator with one or more monomers in the presence of a polymerization catalyst, the low molecular weight initiator having a nominal hydroxyl functionality of at least 2, the one or more monomers being at least one selected from propylene oxide and butylene oxide, and the polymerization catalyst being a Lewis acid catalyst having the general formula $M(R^1)_1(R^2)_1(R^3)_1(R^4)_{0\text{ or }1}$, whereas M is boron, aluminum, indium, bismuth or erbium, $R^1$, $R^2$ and $R^3$ each includes a same fluoroalkyl-substituted phenyl group, and optional $R^4$ includes a functional group or functional polymer group; and
   forming a polyether polyol having a number average molecular weight of greater than the number average molecular weight of the low molecular weight initiator in the presence of the Lewis acid catalyst.

2. The method as claimed in claim 1, wherein the Lewis acid catalyst has the general formula $M(R^1)_1(R^2)_1(R^3)_1(R^4)_{0\text{ or }1}$, whereas M is boron, and each of $R^1$, $R^2$, and $R^3$ is a 3,4- or 3,5-bis(fluoroalkyl)-substituted phenyl group.

3. The method as claimed in claim 1, wherein the Lewis acid catalyst has the general formula $M(R^1)_1(R^2)_1(R^3)_1(R^4)_{0\text{ or }1}$, whereas M is boron, and each of $R^1$, $R^2$, and $R^3$ is a fluoro/chloro-fluoroalkyl-substituted phenyl group, difluoro/chloro-fluoroalkyl-substituted phenyl group, trifluoro/chloro-fluoroalkyl-substituted phenyl group, or tetrafluoro/chloro-fluoroalkyl-substituted phenyl group.

4. The method as claimed in claim 1, wherein the Lewis acid catalyst has the general formula $M(R^1)_1(R^2)_1(R^3)_1(R^4)_1$.

5. The method as claimed in claim 4, wherein $R^4$ is a cyclic ether having 3-10 carbon atoms.

6. The method as claimed in claim 4, wherein $R^4$ is a ketone having 3-10 carbon atoms.

7. The method as claimed in claim 1, wherein the polyether polyol has an acetal content of less than 0.5 mol % based on a total number of moles of the polyether polyol.

8. The method as claimed in claim 1, wherein the low molecular weight initiator is a polyether diol or triol derived from at least one selected from propylene oxide, ethylene oxide, and butylene oxide.

* * * * *